United States Patent
Ho et al.

(10) Patent No.: US 12,220,208 B2
(45) Date of Patent: Feb. 11, 2025

(54) INTELLIGENT EPIDEMIC PREVENTION SYSTEM AND METHOD

(71) Applicant: Acer Incorporated, New Taipei (TW)

(72) Inventors: Andy Ho, New Taipei (TW);
Tsung-Yao Chen, New Taipei (TW);
Cheng-Hung Chen, New Taipei (TW)

(73) Assignee: ACER INCORPORATED, New Taipei (TW)

( * ) Notice: Subject to any disclaimer, the term of this patent is extended or adjusted under 35 U.S.C. 154(b) by 150 days.

(21) Appl. No.: 18/161,979

(22) Filed: Jan. 31, 2023

(65) Prior Publication Data

US 2023/0346228 A1    Nov. 2, 2023

(30) Foreign Application Priority Data

Apr. 28, 2022  (TW) .................................. 111116147

(51) Int. Cl.
| | |
|---|---|
| *A61B 5/01* | (2006.01) |
| *G06T 7/80* | (2017.01) |
| *G06V 40/10* | (2022.01) |
| *G06V 40/16* | (2022.01) |
| *G06V 40/70* | (2022.01) |
| *G07C 9/00* | (2020.01) |
| *G16H 50/80* | (2018.01) |
| *H04N 23/11* | (2023.01) |

(52) U.S. Cl.
CPC ................ *A61B 5/015* (2013.01); *G06T 7/80* (2017.01); *G06V 40/15* (2022.01); *G06V 40/171* (2022.01); *G06V 40/70* (2022.01); *G07C 9/00563* (2013.01); *G16H 50/80* (2018.01); *H04N 23/11* (2023.01); *A61B 2560/0223* (2013.01); *G06T 2207/10048* (2013.01); *G06T 2207/30196* (2013.01); *G06T 2207/30244* (2013.01)

(58) Field of Classification Search
CPC ............ A61B 2560/0223; A61B 5/015; G06T 2207/10048; G06T 2207/30196; G06T 2207/30244; G06T 7/80; G06V 10/19; G06V 10/803; G06V 2201/02; G06V 40/10; G06V 40/15; G06V 40/171; G06V 40/70; G07C 9/00; G07C 9/00563; G16H 30/40; G16H 40/20; G16H 50/80; H04N 23/11
USPC .......................................................... 348/77
See application file for complete search history.

(56) References Cited

U.S. PATENT DOCUMENTS

2023/0043342 A1* 2/2023 Tremblay ............. H04N 23/698

* cited by examiner

*Primary Examiner* — Kathleen M Walsh
(74) *Attorney, Agent, or Firm* — McClure, Qualey & Rodack, LLP

(57) ABSTRACT

An intelligent epidemic prevention system includes a calibration device, an access control system, a visible-light camera recording a first calibration device image of the calibration device and a first user image of a user, a thermographic camera recording a second calibration device image of the calibration device and a second user image of the user, and a computing device that calculates a calibration value according to the first and second calibration device images. The computing device determines whether the user wears a mask properly according to the first user image and generates a first result, and determines whether the temperature of the user is greater than or equal to a threshold temperature according to the calibration value and the second user image and generates a second result. The computing device controls the access control system to open or close according to the first and second results.

10 Claims, 6 Drawing Sheets

INTELLIGENT EPIDEMIC PREVENTION SYSTEM AND METHOD

CROSS REFERENCE TO RELATED APPLICATIONS

This application claims priority of Taiwan Patent Application No. 111116147, filed on Apr. 28, 2022, the entirety of which is incorporated by reference herein.

BACKGROUND OF THE INVENTION

Field of the Invention

The present disclosure relates to an intelligent epidemic prevention system, and, in particular, to an intelligent epidemic prevention system that monitors the body temperature and the mask wearing of a user.

Description of the Related Art

With the prevalence of infectious diseases such as COVID-19, people must measure body temperature and wear masks when entering and leaving public places to reduce the possibility of disease transmission. Therefore, checkpoints are often set up at the entrances and exits of public places (such as the gates of public transportation systems) to measure the body temperature and check that people are wearing masks when entering and exiting.

Therefore, we urgently need an intelligent epidemic prevention system that can accurately and effectively automatically check the body temperature and mask wearing of people entering and exiting, and combine it with the entrance and exit access control system and data analysis system to improve the effect of disease prevention and maintain the health of people.

BRIEF SUMMARY OF THE INVENTION

The term "embodiment" and like terms (such as "implementation", "configuration", "aspect", "example", and "option") are intended to refer broadly to all of the subject matter of this disclosure and the claims below. Statements containing these terms should be understood not to limit the subject matter described herein or to limit the meaning or scope of the claims below. Embodiments of the present disclosure covered herein are defined by the claims below, supplemented by this summary. This summary is a high-level overview of various aspects of the disclosure and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this disclosure, any or all drawings and each claim.

An embodiment of the present disclosure provides an intelligent epidemic prevention system, including: a calibration device having a metal plate, wherein the metal plate is heated to a predetermined sensing temperature; an access control system; a visible-light camera recording a first calibration device image of the calibration device and a first user image of a user; a thermographic camera recording a second calibration device image of the calibration device and a second user image of the user; and a computing device calculating a first position of the calibration device on the first calibration device image and a second position of the calibration device on the second calibration device image, calculating a base-corresponding position of the calibration device on the second calibration device image according to the first position, and calculating a calibration value according to the second position and the base-corresponding position; wherein the computing device determines whether the user is wearing a mask properly according to the first user image and generates a first result, and determines whether a body temperature of the user is greater than or equal to a threshold temperature according to the calibration value and the second user image and generates a second result; wherein the computing device controls the access control system to open or close according to the first result and the second result.

Another embodiment of the present disclosure provides an intelligent epidemic prevention method. The method includes recording a first calibration device image of a calibration device with a visible-light camera. The calibration device has a metal plate heated to a predetermined sensing temperature. The method includes recording a second calibration device image of the calibration device with a thermographic camera; calculating a first position of the calibration device on the first calibration device image and a second position of the calibration device on the second calibration device image; calculating a base-corresponding position of the calibration device on the second calibration device image according to the first position, and calculating a calibration value according to the second position and the base-corresponding position; recording a first user image of a user with the visible-light camera; recording a second user image of the user with the thermographic camera; determining whether the user is wearing a mask properly according to the first user image and generating a first result, and determining whether a body temperature of the user is greater than or equal to a threshold temperature according to the calibration value and the second user image and generating a second result; and controlling a access control system to open or close according to the first result and the second result.

The above summary is not intended to represent each embodiment or every aspect of the present disclosure. Rather, the foregoing summary merely provides an example of some of the novel aspects and features set forth herein. The above features and advantages, and other features and advantages of the present disclosure, will be readily apparent from the following detailed description of representative embodiments and modes for carrying out the present invention, when taken in connection with the accompanying drawings and the appended claims. The additional aspects of the present disclosure will be readily apparent to those skilled in the art from the following various embodiments in the "Detailed Description of the Invention", when taken in connection with the drawings. A brief description of the drawings is set out in the section headed "Brief Description of the Drawings" below.

BRIEF DESCRIPTION OF THE DRAWINGS

The present disclosure can be more fully understood by reading the subsequent detailed description and examples with references made to the accompanying drawings.

Understanding that these drawings depict only exemplary aspects of the disclosure and are not therefore to be considered to be limiting of its scope.

Figure 1:
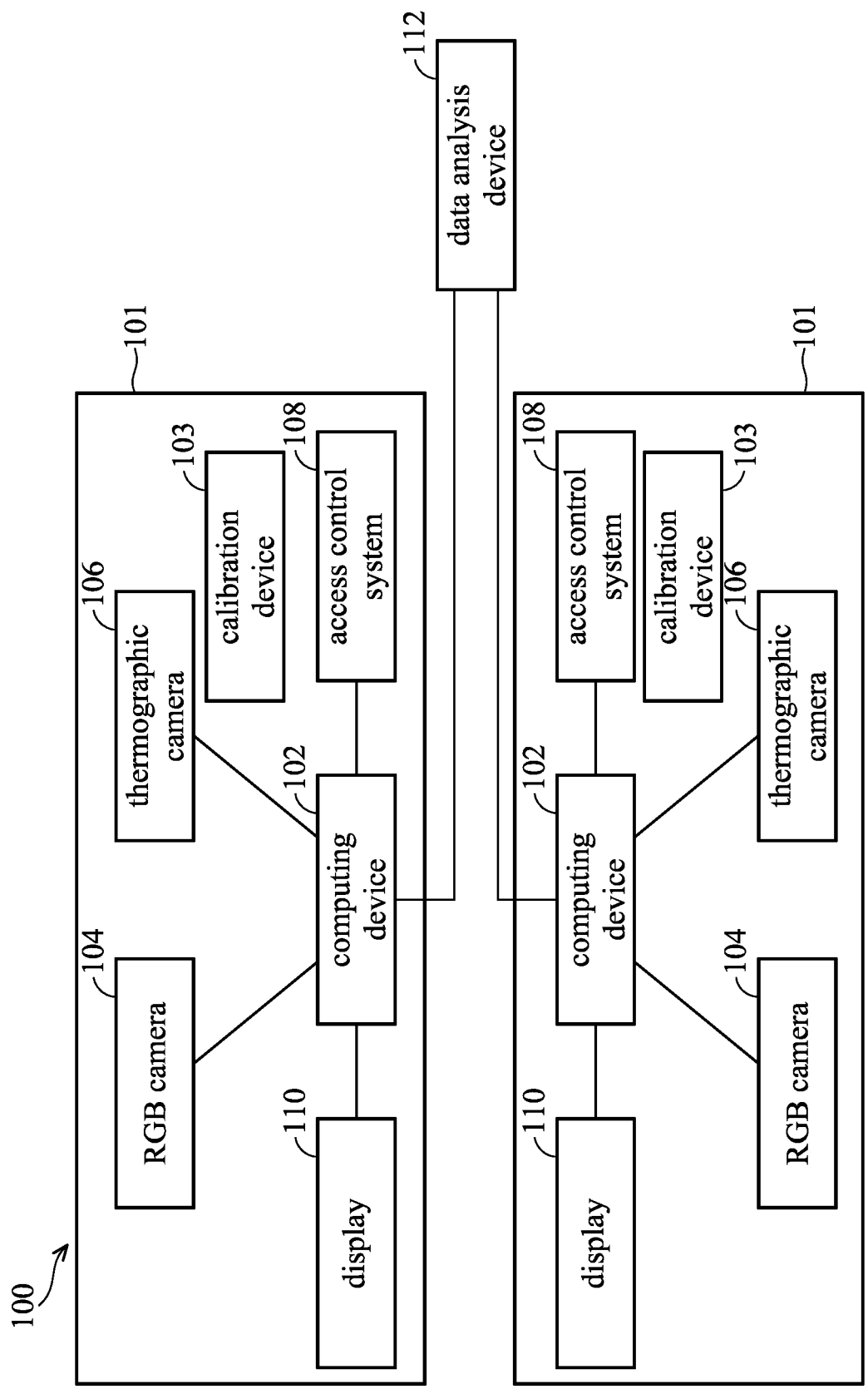
FIG. 1 is a block diagram showing an intelligent epidemic prevention system.

The present disclosure is susceptible to various modifications and alternative forms. Some representative embodiments have been shown by way of example in the drawings and will be described in detail herein. It should be understood, however, that the disclosure is not intended to be limited to the particular forms disclosed. Rather, the disclosure is to cover all modifications, equivalents, and alternatives falling within the spirit and scope of the disclosure as defined by the appended claims.

DETAILED DESCRIPTION OF THE INVENTION

The present disclosure provides many different embodiments, or examples, for implementing different features of this disclosure. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "above", "below", "front", "behind" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

FIG. 1 is a block diagram showing an intelligent epidemic prevention system. In FIG. 1, the intelligent epidemic prevention system 100 includes at least one epidemic prevention device 101, wherein each of the epidemic prevention devices 101 includes a computing device 102. The computing device 102 may be, for example, a central processing unit (CPU), a microcontroller (MCU), a system on a chip (SoC), a digital signal processor (DSP), an application-specific integrated circuit (ASIC), a programmable logic device (PLD), a field programmable logic device (FPLD), a field programmable logic gate array (FPGA), a discrete logic device, or any other suitable computing device. The computing device 102 may also be a personal computer, a server, a workstation, or any other suitable computing device including the above components. Each of the epidemic prevention device 101 also includes a visible-light camera, such as a red-green-blue (RGB) camera 104. In the following, the RGB camera 104 will be used as an example for illustration, but the disclosure is not limited thereto. Each of the epidemic prevention device 101 also includes a thermographic camera 106 (such as but not limited to an infrared thermography camera), an access control system 108 (such as but not limited to a gate system of a public transportation system), and a display 110 (such as but not limited to a liquid crystal display (LCD)). The RGB camera 104, the thermographic camera 106, the access control system 108, and the display 110 in each of the epidemic prevention device 101 are coupled to the computing device 102 in the epidemic prevention device 101. Each of the epidemic prevention device 101 is coupled to a data analysis device 112. The data analysis device 112 may be located at the outside of the epidemic prevention device 101 (but not limited thereto), such as (but not limited to) in a traffic control center of the public transportation system. The data analysis device 112 may be, for example, a personal computer, a server, a workstation, or any other suitable computing device.

Each of the epidemic prevention devices 101 of the intelligent epidemic prevention system 100 may detect whether the body temperature of the user (such as a passenger entering a public transportation system) is normal, and whether the user is wearing a mask properly, and determine whether to allow the user to pass through the access control system 108 according to the body temperature and the mask wearing of the user. Firstly, the display 110 displays a message to instruct the user to wear the mask properly so as to receive measurements from the RGB camera 104 and the thermographic camera 106. Subsequently, the RGB camera 104 records a first user image of the user (e.g., a visible light image), and the thermographic camera 106 records a second user image of the user (e.g., a thermal image). The computing device 102 analyzes the first user image through image recognition technology (such as deep learning technology, etc.) to detect a face position of the user and determine whether the user is wearing the mask properly. Then, according to the above face position of the user, the computing device 102 analyzes whether a temperature of the face position in the second user image (i.e., the body temperature of the user) is greater than or equal to a threshold temperature (e.g., 37.5 degrees Celsius). At this time, the display 110 displays the body temperature and the mask wearing of the user determined by the computing device 102. If the user is wearing the mask properly and the body temperature is lower than the threshold temperature, the access control system 108 opens to allow the user to pass through the access control system 108. If the user wears the mask improperly or the body temperature is greater than or equal to the threshold temperature, the access control system 108 closes and the user is prohibited from passing through the access control system 108. At this time, the display 110 displays a message to instruct the user to wear the mask again or the body temperature is abnormal.

Figure 2B:
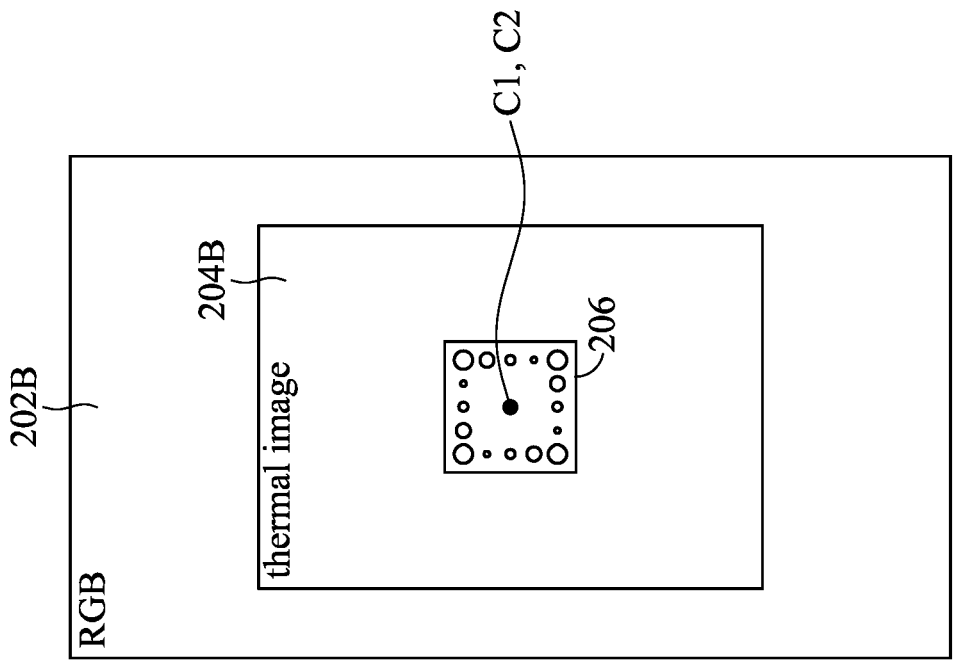
FIG. 2B is a schematic diagram showing an example of imaging ranges of the RGB camera and the thermographic camera after calibration.
Figure 2A:
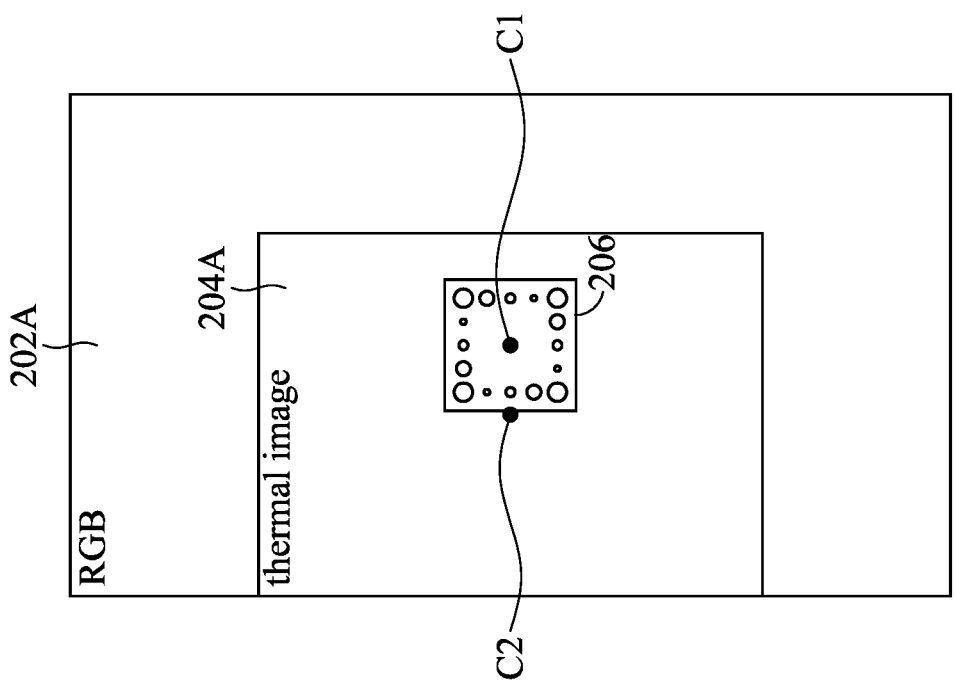
FIG. 2A is a schematic diagram showing an example of imaging ranges of a RGB camera and a thermographic camera before calibration.

In some embodiments, the epidemic prevention device 101 includes a calibration device 103. In the epidemic prevention device 101, there are the RGB camera 104 and the thermographic camera 106. These two cameras may have errors in imaging ranges when the hardware is set up, resulting in inconsistent face positions in the image recorded by the RGB camera 104 and the face position in the image recorded by the thermographic camera 106, thereby affecting the monitoring accuracy of the epidemic prevention device 101. In order to improve such situation, the imaging ranges of the RGB camera 104 and the thermographic camera 106 must be calibrated. Referring to FIG. 2A, a center point C1 of a first imaging range 202A of the RGB camera 104 and a center point C2 of a second imaging range 204A of the thermographic camera 106 are not aligned. In order to calibrate such error, the calibration device 103 may be placed at an appropriate distance (e.g., 30 to 50 centimeters) from the RGB camera 104 and the thermographic camera 106. Using the imaging positions of the calibration device 103 on the RGB camera 104 and the thermographic camera 106, the first imaging range 202A and the second imaging range 204A are calibrated so that the center points C1 and C2 are aligned. FIG. 2B shows the state after the calibration is completed. At this time, the center point C1 of a first imaging range 202B of the RGB camera 104 and the center point C2 of a second imaging range 204B of the thermographic camera 106 are aligned.

In this embodiment, the calibration device 103 includes a metal plate 206, which can be made of aluminum, iron, stainless steel or other suitable materials. The advantage of using a metal plate is that it is easy to heat, which facilitates imaging by the thermographic camera 106. The metal plate 206 has an appropriate size (e.g., a square with a side length of 30 cm), and is placed in an intersection area of the first imaging range 202A of the RGB camera 104 and the second imaging range 204A of the thermographic camera 106, so that the RGB camera 104 and the thermographic camera 106 may both record the image of the metal plate 206. In this embodiment, the metal plate 206 has a plurality of hollow geometric patterns (such as but not limited to those shown in FIG. 2A and FIG. 2B) to facilitate the computing device 102 to identify the position of the metal plate 206 in the first imaging range of the RGB camera 104. For example, in some embodiments, the calibration device 103 further includes a heater (not shown in the figure) for heating the metal plate 206 to a predetermined sensing temperature to facilitate the computing device 102 to identify the position of the metal plate 206 in the second imaging range of the thermographic camera 106. In some embodiments, the predetermined sensing temperature is higher than room temperature (e.g., 30-40 degrees Celsius).

Figure 3A:
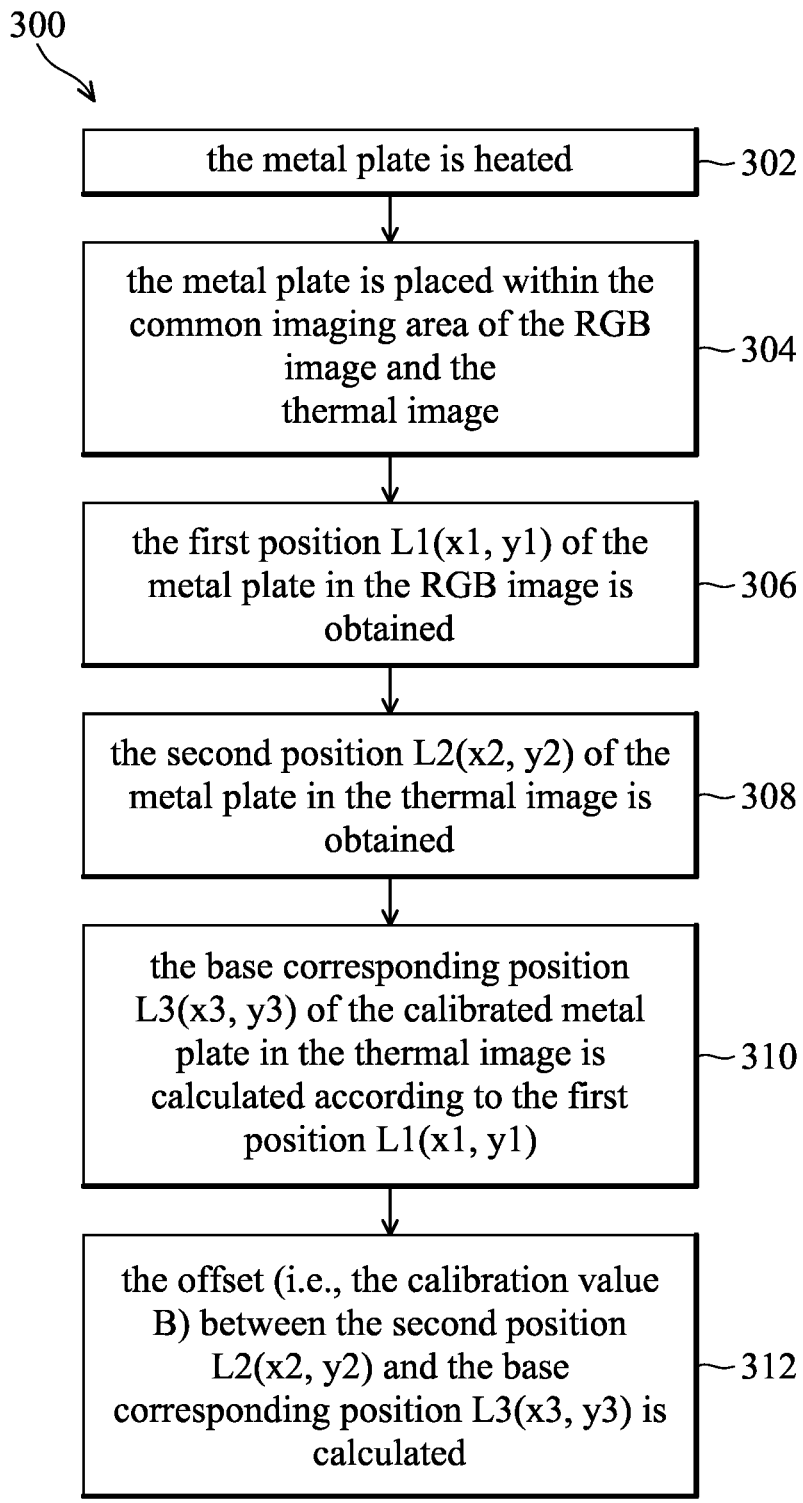
FIG. 3A is a flowchart showing a camera calibration method applicable to the RGB camera and the thermographic camera shown in FIG. 2A.
Figure 3B:
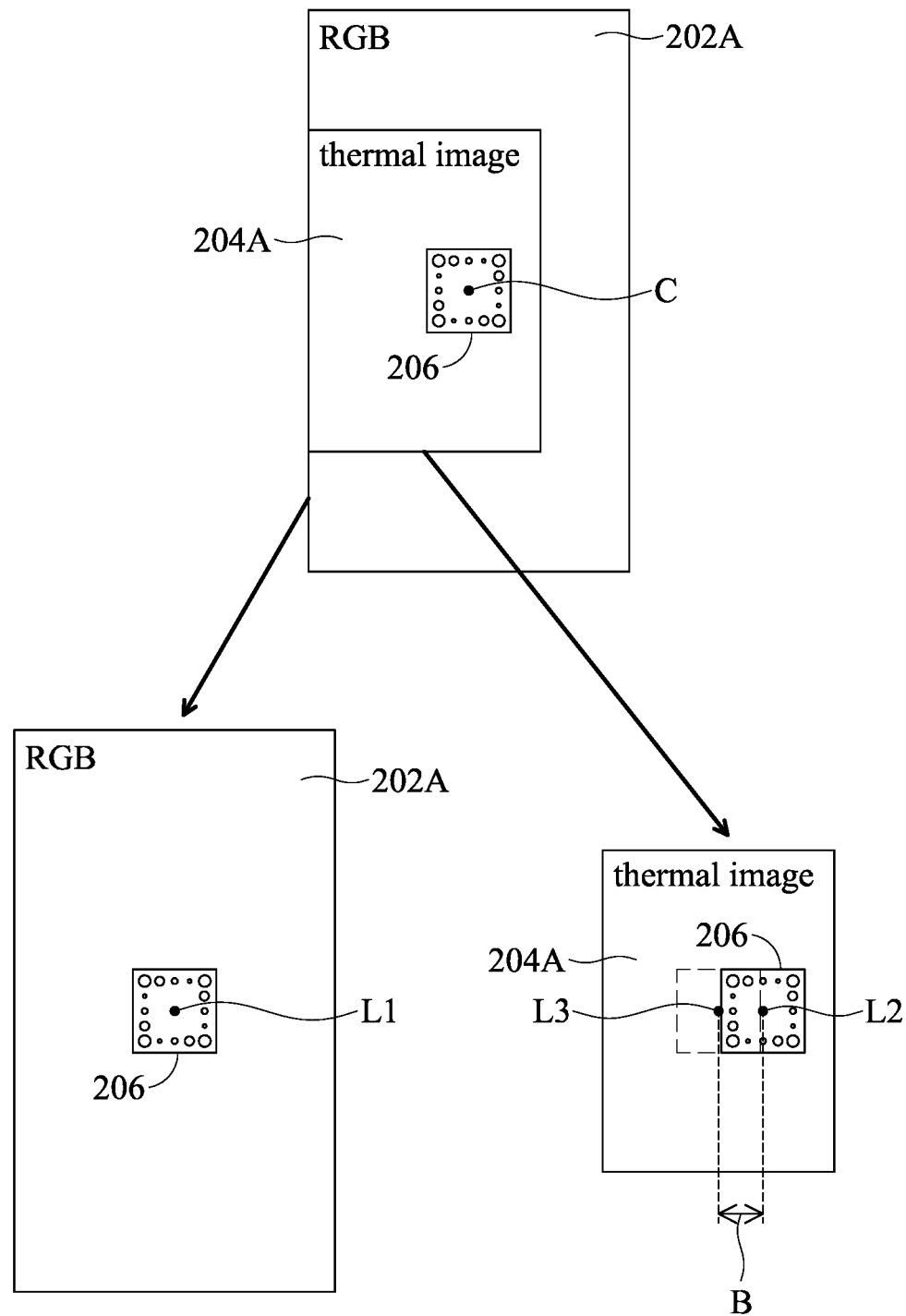
FIG. 3B is a schematic diagram showing a calculation process of the camera calibration method in FIG. 3A.

FIG. 3A is a flowchart showing a method 300 for calibrating the imaging ranges of the RGB camera 104 and the thermographic camera 106, so that their center points C1 and C2 are aligned. In step 302, the metal plate 206 (such as an aluminum plate) is heated to a predetermined sensing temperature to for imaging and identification by the thermographic camera 106. In step 304, the metal plate 206 (such as an aluminum plate) is placed within the intersection area (or common imaging area) of the first imaging range 202A of the RGB camera 104 and the second imaging range 204A of the thermographic camera 106, so that the RGB camera 104 and the thermographic camera 106 may both record the image of the metal plate 206. At this time, the RGB camera 104 records a first calibration device image of the metal plate 206, and the thermographic camera 106 records a second calibration device image of the metal plate 206. In step 306, the computing device 102 calculates a first position L1(x1, y1) of a positioning point on the metal plate 206 (e.g., a center point C of the metal plate) on the first calibration device image (RGB image) according to the first calibration device image. In some embodiments, since the metal plate 206 is rectangular, according to the first calibration device image, the computing device 102 calculates the position of a vertex of the metal plate 206 on the first calibration device image as the first position L1(x1, y1), or the position of a specific hollow geometric pattern in the metal plate 206 on the first calibration device image as the first position L1(x1, y1). In step 308, according to the second calibration device image, the computing device 102 uses an algorithm to calculate (convert) a second position L2(x2, y2) of the positioning point on the metal plate 206 (e.g., the center point C of the metal plate) on the second calibration device image (thermal image). In some embodiments, since the metal plate 206 is rectangular, according to the second calibration device image, the computing device 102 calculates the position of the vertex of the metal plate 206 on the second calibration device image as the second position L2(x2, y2), or the position of the specific hollow geometric pattern in the metal plate 206 on the second calibration device image as the second position L2(x2, y2). Since the imaging ranges of the RGB camera 104 and the thermographic camera 106 are not necessarily equal (e.g., the RGB camera 104 may have an imaging range of 1080 pixels*1920 pixels, while the thermographic camera 106 may have an imaging range of 960 pixels*1280 pixels), so that the imaging ranges of the RGB camera 104 and the thermographic camera 106 correspond to each other according to a mapping relationship. Referring to FIGS. 2A and 3B, when the center points C1 and C2 of the first imaging range 202A of the RGB camera 104 and the second imaging range 204A of the thermographic camera 106 are not aligned, the relative position of the center point C of the metal plate 206 within the first imaging range 202A and the second imaging range 204A will have a mapping relationship (or algorithm) F 1; for example, when the metal plate 206 is placed in the center of the first imaging range 202A, the first position L1(x1, y1) falls in the center of the first imaging range 202A, but the second position L2(x2, y2) is not in the center of the second imaging range 204A.

At this time, in step 310, according to the first position L1(x1, y1) of the center point C of the metal plate 206 on the first calibration device image, the computing device 102 calculates (converts) a base-corresponding position L3(x3, y3) of the center point C of the metal plate 206 on the second imaging range 204A of the thermographic camera 106 using the mapping relationship F1.

In step 312, the computing device 102 calculates an offset between the base-corresponding position L3(x3, y3) of the metal plate 206 and the current position (that is, the second position L2(x2, y2)) on the second imaging range 204A, i.e., (x3-x2, y3-y2). The computing device 102 uses the offset as a calibration value B of the second imaging range 204A of the thermographic camera 106. In other words, when the computing device 102 subsequently converts each of pixels in the first imaging range 202A into each of pixels in the second imaging range 204A of the thermographic camera 106, it will be calibrated with the calibration value B to obtain a calibrated pixel point on the second imaging range 204B, and then aligns the center points C1 and C2 of the imaging ranges of the RGB camera 104 and the thermal imaging camera 106, as shown in FIG. 2B. At this time, the relative position of the metal plate 206 within the first imaging range 202B and the second imaging range 204B have a calibrated mapping relationship. For example, when the metal plate 206 is placed at the center of the first imaging range 202B, the center point of the metal plate 206 falls on the center point C1 of the first imaging range 202B and the center point C2 of the second imaging range 204B. It should be noted that the calibration value B is a vector. The magnitude and direction of the calibration value B shown in FIG. 3B is an example for convenience of illustration only, and the calibration value B may have any suitable magnitude and direction. For example, the calibration value B shown in FIG. 3B has a displacement in the horizontal direction, and the calibration value B may have any suitable horizontal displacement and vertical displacement.

The method 300 is performed once during hardware set or troubleshooting, and does not need to be performed before each measurement for the user. After the method 300 is completed, when the computing device 102 converts any pixel in the first imaging range 202A of the RGB camera 104 (of the user image) into a pixel in the second imaging range 204A of the thermographic camera 106 each time in the future, the computing device 102 calibrates the obtained corresponding result with the stored calibration value B. When there are other heat sources near the user's face (such as hot drinks, warm packs, etc.), the thermographic camera 106 may record these external heat sources and misjudge that the body temperature of the user is too high. In order to solve this problem, it may further determine the area that actually belongs to the user's face in the calibrated second user image by detecting facial key points (such as eyes and forehead) in the first user image.

Figure 3C:
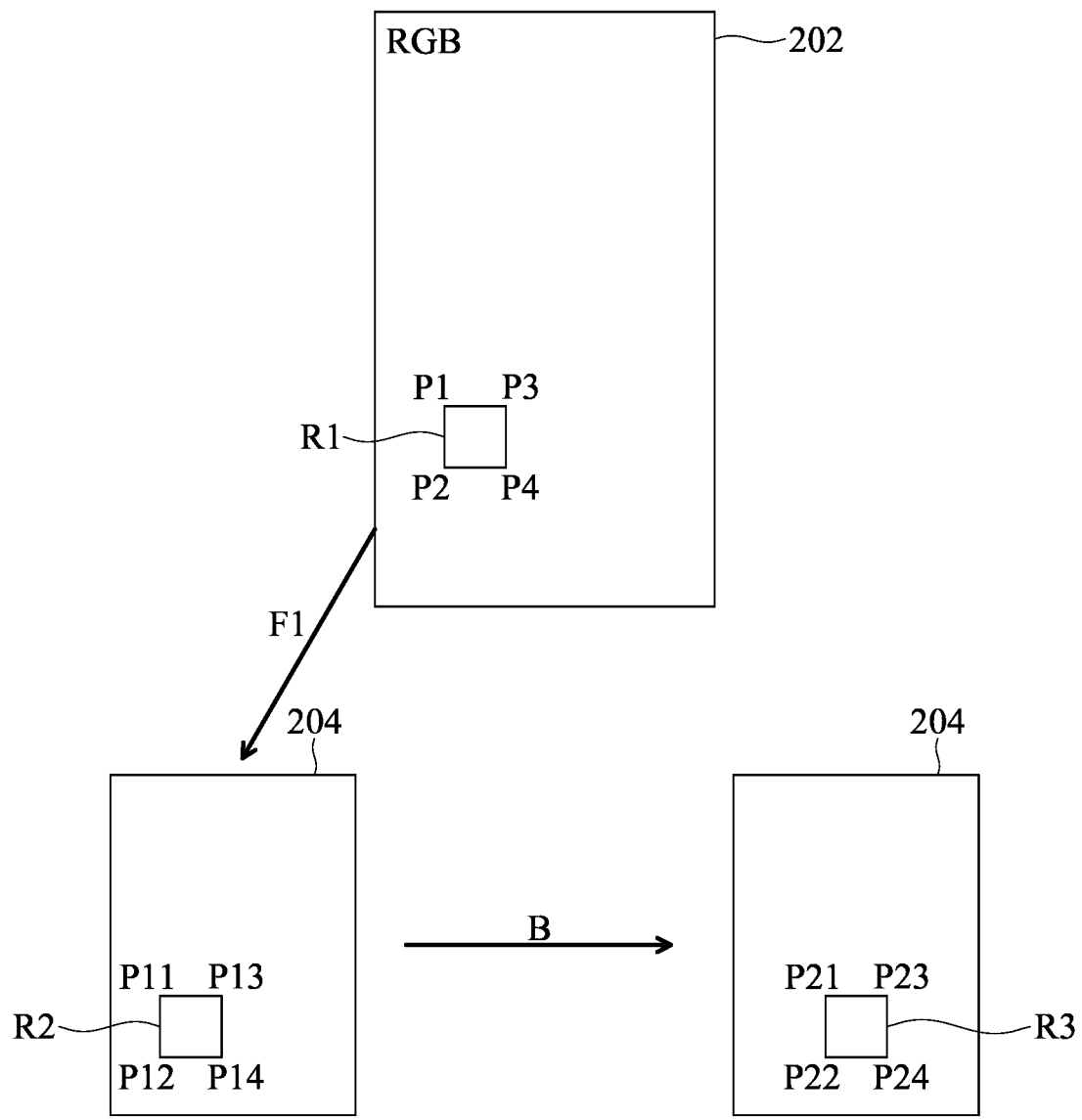
FIG. 3C is a schematic diagram showing the calculation process of calibrating a face area of a user image using a calibration value obtained by the camera calibration method in FIGS. 3A and 3B.

In detail, the computing device 102 detects the facial key points in the first user image (such as RGB image) through image recognition technology (such as deep learning) to capture a face are in the first user image, such as an area R1 in FIG. 3C, and the area R1 has four corner positions P1-P4. In the present embodiment, a first imaging range 202 in FIG. 3C is the imaging range of a user image, and a second imaging range 204 is the thermal imaging range of the user image. The computing device 102 converts the four corner positions P1-P4 into corresponding positions in the second imaging range 204 of the thermographic camera 106 using the mapping relationship F1 to obtain a base-corresponding area in the second imaging range 204, such as an area R2. Corner positions P11-P14 of the area R2 are base-corresponding positions of the corner positions P1-P4 on the second imaging range 204. Subsequently, the computing device 102 uses the calibration value (offset) B to calibrate the position of the base-corresponding area R2 (e.g., the corner positions P11-P14) to obtain a calibrated corresponding area R3 in the second imaging range 204. Corner positions P21-P24 of the area R3 are calibrated corresponding positions of the corner positions P11-P14 on the second imaging range 204. When the temperature in the calibrated corresponding area R3 is greater than or equal to the threshold temperature, the computing device 102 determines that the body temperature of the user is greater than or equal to the threshold temperature. In some embodiments, the computing device 102 may determine that the body temperature of the user is greater than or equal to the threshold temperature by the average temperature or the highest temperature of the temperatures in the calibrated corresponding area R3. In some embodiments, when the user is wearing the mask, the facial key points may include characteristic parts such as eyes and forehead. When no characteristic parts such as eyes and forehead are detected, the computing device 102 may control the display 110 to display a message, instructing the user to expose the facial key points to prevent the facial key points from being covered by external heat sources, thereby affecting the body temperature determination result of the computing device 102.

Figure 4:
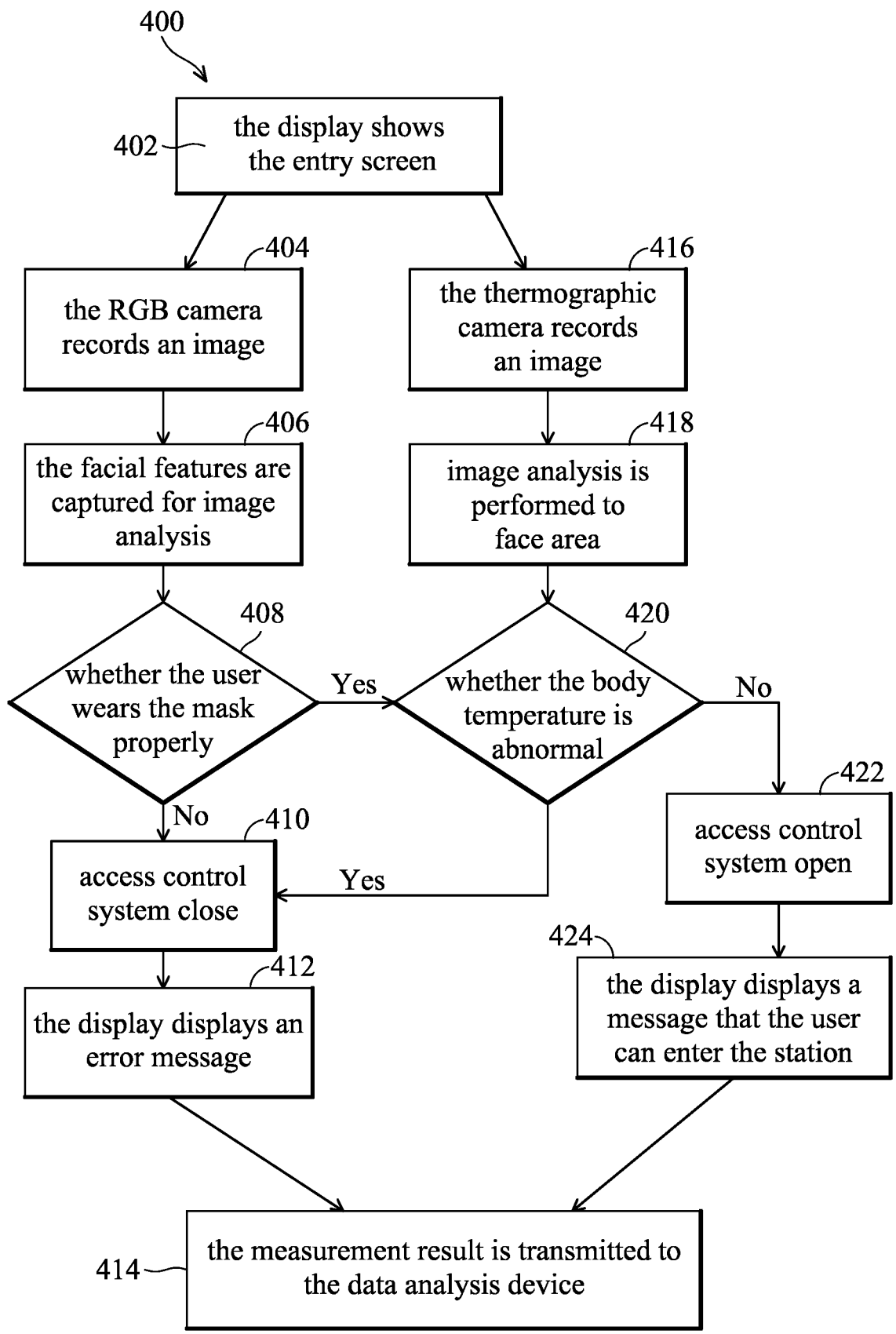
FIG. 4 is a flowchart showing an automated people monitoring method, which is applicable to the intelligent epidemic prevention system shown in FIG. 1.

FIG. 4 is a flowchart showing an automated people monitoring method, which is applicable to the intelligent epidemic prevention system shown in FIG. 1. Before a method 400 shown in FIG. 4 is performed, the method 300 shown in FIG. 3A is performed once to obtain the calibration value B. In FIG. 4, the method 400 starts from step 402. At this time, the display 110 displays a message instructing the user to wear the mask properly and to expose the facial key points for recording by the RGB camera 104 and the thermographic camera 106. Subsequently, in step 404, the RGB camera 104 records a first user image (not shown) of the user and sends it to the computing device 102. In step 406, the computing device 102 captures the facial features of the user in the first user image, captures the face area (such as the area R1 in FIG. 3C) in the first user image, and analyzes the mask wearing of the user in the face area through image recognition technology (such as deep learning). Meanwhile, in step 416, the thermographic camera 106 records a second user image (not shown) of the user and sends it to the computing device 102. In step 418, the computing device 102 analyzes the calibrated corresponding area corresponding to the face area obtained in step 406 in the second user image (i.e., in the thermal imaging range of the thermographic camera 106). For example, the computing device 102 calculates a basic corresponding area (such as the area R2 in FIG. 3C) of the face area (such as the area R1 in FIG. 3C) obtained in step 406 in the second user image (i.e., in the thermal imaging range of the thermographic camera 106), and uses the calibration value B to calibrate the position of the basic corresponding area (e.g., the area R2 in FIG. 3C) to obtain a calibrated corresponding area (e.g., the area R3) in the second user image (i.e., in the thermal imaging range of the thermographic camera 106). When the temperature (average temperature or maximum temperature) in the calibrated corresponding area R3 is greater than or equal to the threshold temperature, the computing device 102 determines that the body temperature of the user is greater than or equal to the threshold temperature.

In step 408, the computing device 102 determines whether the user is wearing the mask properly according to the analysis result in step 406. If yes, in step 420, the computing device 102 determines whether the body temperature of the user is abnormal (greater than or equal to the threshold temperature) according to the analysis result in step 418. If no, then in step 422, the computing device 102 controls the access control system 108 to open to allow the user to pass through, and in step 424, the display 110 displays a message that the user can enter the station. In other words, when the user is wearing the mask properly and the body temperature is lower than the threshold temperature, the access control system 108 open. Subsequently, in step 414, the computing device 102 transmits the measurement result to the data analysis device 112 for subsequent data analysis.

If in step 408, the user wears the mask improperly, or in step 420, the body temperature of the user is abnormal, then in step 410, the computing device 102 controls the access control system 108 to close, prohibiting the user from passing through, and in step 412, the display 110 displays an error message that the user is prohibited from entering the station. In other words, when the user is wearing the mask improperly, or the body temperature is greater than or equal to the threshold temperature, the access control system 108 close. Subsequently, in step 414, the computing device 102 transmits the measurement result to the data analysis device 112 for subsequent data analysis.

The aforementioned measurement results sent to the data analysis device 112 represent user information of a single user; the data analysis device 112 may analyze the user information from different epidemic prevention devices 101 (e.g., big data analysis) for relevant personnel to monitor the mask wearing and the distribution of the number of people with fever of users in various places (such as passengers at various stations of the public transportation system), to take relevant measures in time to prevent the spread of the disease. Specifically, the user information may include a first signal and a second signal, in which the first signal indicates whether the body temperature of the user is greater than or equal to the threshold temperature, and the second signal indicates whether the user is wearing the mask properly. The data analysis device 112 generates an analysis result according to the user information. Such analysis result may include a distribution of the first signal and the second signal at different stations, that is, the distribution of the number of people with fever and the distribution of the mask wearing at various stations. Each of the epidemic prevention devices 101 may record the daily number of people who are prohibited from entering the station due to abnormal body temperature, and provide this data to the data analysis device 112. The data analysis device 112 may display the distribution of the number of people with fever and the distribution of the mask wearing at various stations through, for example, the graphical interface. Relevant personnel may use the graphical interface to know whether the number and proportion of the number of people with fever at various stations are abnormally high or whether there is regional correlation. The graphical interface may also be combined with other epidemic prevention information (such as confirmed footprints) to display hot zone warnings, and issue clearance notifications and hierarchical notifications, so that relevant personnel may take timely measures to prevent the spread of the disease.

The foregoing description of the embodiments, including illustrated embodiments, has been presented only for the purpose of illustration and description and is not intended to be exhaustive or limiting to the precise forms disclosed. Numerous modifications, adaptations, and uses thereof will be apparent to those skilled in the art. Numerous changes to the disclosed embodiments can be made in accordance with the disclosure herein, without departing from the spirit or scope of the disclosure. Thus, the breadth and scope of the present disclosure should not be limited by any of the above described embodiments.

Although certain aspects and features of the present disclosure have been illustrated and described with respect to one or more implementations, equivalent alterations and modifications will occur or be known to others skilled in the art upon the reading and understanding of this specification and the annexed drawings. In addition, while a particular feature of the disclosure may have been disclosed with respect to only one of several implementations, such feature may be combined with one or more other features of the other implementations as may be desired and advantageous for any given or particular application.

The terminology used herein is for the purpose of describing particular embodiments only, and is not intended to be limiting of the disclosure. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

What is claimed is:

1. An intelligent epidemic prevention system, comprising:
    a calibration device having a metal plate, wherein the metal plate is heated to a predetermined sensing temperature;
    an access control system;
    a visible-light camera recording a first calibration device image of the calibration device and a first user image of a user;
    a thermographic camera recording a second calibration device image of the calibration device and a second user image of the user; and
    a computing device calculating a first position of the calibration device on the first calibration device image and a second position of the calibration device on the second calibration device image, calculating a base-corresponding position of the calibration device on the second calibration device image according to the first position, and calculating a calibration value according to the second position and the base-corresponding position;
    wherein the computing device determines whether the user is wearing a mask properly according to the first user image and generates a first result, and determines whether a body temperature of the user is greater than or equal to a threshold temperature according to the calibration value and the second user image and generates a second result;
    wherein the computing device controls the access control system to open or close according to the first result and the second result.

2. The intelligent epidemic prevention system as claimed in claim 1, wherein the predetermined sensing temperature is greater than a room temperature and the metal plate has hollow geometric patterns.

3. The intelligent epidemic prevention system as claimed in claim 1, wherein:
    the computing device controls the access control system to open in response to the user wearing the mask properly and the body temperature being lower than the threshold temperature; and
    the computing device controls the access control system to close in response to the user wearing the mask improperly or the body temperature being greater than or equal to the threshold temperature.

4. The intelligent epidemic prevention system as claimed in claim 3, wherein:
    the computing device captures a face area in the first user image by detecting facial key points in the first user image; the computing device calculates a base-corresponding area of the face area in the second user image and calibrates a position of the base-corresponding area with the calibration value to obtain a calibrated corresponding area in the second user image, and the computing device determines that the body temperature of the user is greater than or equal to the threshold temperature when a temperature in the calibrated corresponding area is greater than or equal to the threshold temperature.

5. The intelligent epidemic prevention system as claimed in claim 1, further comprising a data analysis device coupled to the computing device;
the computing device transmits user information to the data analysis device in response to the opening or closing of the access control system; and
the data analysis device generates an analysis result according to the user information;
wherein the user information comprises:
a first signal indicating whether the body temperature of the user is greater than or equal to the threshold temperature; and
a second signal indicating whether the user is wearing the mask properly; and
wherein the analysis result comprises a distribution of the first signal and the second signal at different stations.

6. An intelligent epidemic prevention method, comprising:
recording a first calibration device image of a calibration device with a visible-light camera, wherein the calibration device has a metal plate heated to a predetermined sensing temperature;
recording a second calibration device image of the calibration device with a thermographic camera;
calculating a first position of the calibration device on the first calibration device image and a second position of the calibration device on the second calibration device image;
calculating a base-corresponding position of the calibration device on the second calibration device image according to the first position, and calculating a calibration value according to the second position and the base-corresponding position;
recording a first user image of a user with the visible-light camera;
recording a second user image of the user with the thermographic camera;
determining whether the user is wearing a mask properly according to the first user image and generating a first result, and determining whether a body temperature of the user is greater than or equal to a threshold temperature according to the calibration value and the second user image and generating a second result; and
controlling an access control system to open or close according to the first result and the second result.

7. The intelligent epidemic prevention method as claimed in claim 6, wherein the predetermined sensing temperature is greater than a room temperature and the metal plate has hollow geometric patterns.

8. The intelligent epidemic prevention method as claimed in claim 6, wherein:
the access control system opens when the user is wearing the mask properly and the body temperature is lower than the threshold temperature; and
the access control system closes when the user is wearing the mask improperly or the body temperature is greater than or equal to the threshold temperature.

9. The intelligent epidemic prevention method as claimed in claim 8, wherein the operations of determining whether the user is wearing the mask properly and determining whether the body temperature of the user is greater than or equal to the threshold temperature include:
capturing a face area in the first user image by detecting facial key points in the first user image;
calculating a base-corresponding area of the face area in the second user image and calibrating a position of the base-corresponding area with the calibration value to obtain a calibrated corresponding area in the second user image; and
when a temperature in the calibrated corresponding area is greater than or equal to the threshold temperature, the computing device determines that the body temperature of the user is greater than or equal to the threshold temperature.

10. The intelligent epidemic prevention method as claimed in claim 6, further comprising:
generating user information in response to the opening or closing of the access control system; and
generating an analysis result according to the user information;
wherein the user information comprises:
a first signal indicating whether the body temperature of the user is greater than or equal to the threshold temperature; and
a second signal indicating whether the user is wearing the mask properly; and
wherein the analysis result comprises a distribution of the first signal and the second signal at different stations.

* * * * *